(12) United States Patent
LeMay et al.

(10) Patent No.: US 7,044,928 B2
(45) Date of Patent: May 16, 2006

(54) TAMPON APPLICATOR ASSEMBLY HAVING AN IMPROVED PLUNGER AND METHODS OF MAKING

(75) Inventors: Jessica LeMay, New Castle, DE (US); Keith J. Edgett, Middletown, DE (US); Kathryn G. Bennett, Fairfield, CT (US); Wayne David Melvin, Camden, DE (US)

(73) Assignee: Platex Products, Inc., Westport, CT (US)

( * ) Notice: Subject to any disclaimer, the term of this patent is extended or adjusted under 35 U.S.C. 154(b) by 102 days.

(21) Appl. No.: 10/407,861

(22) Filed: Apr. 4, 2003

(65) Prior Publication Data

US 2004/0199100 A1  Oct. 7, 2004

(51) Int. Cl.
  *A61F 13/20* (2006.01)
(52) U.S. Cl. .............................. 604/15; 604/11; 604/14
(58) Field of Classification Search ........... 604/11–18; D24/141
  See application file for complete search history.

(56) References Cited

U.S. PATENT DOCUMENTS

| | | | | |
|---|---|---|---|---|
| 1,794,221 A * | 2/1931 | Washburn et al. | ............. | 604/15 |
| 1,969,671 A | 8/1934 | Nelson | ......... | 128/263 |
| D98,874 S | 3/1936 | Lewis | | |
| D103,976 S | 4/1937 | Lermer | | |
| 2,298,752 A | 10/1942 | Crockford | ............. | 128/263 |
| 2,476,956 A * | 7/1949 | Bonham | ......... | 604/15 |
| 2,739,593 A | 3/1956 | McLaughlin | ............. | 128/263 |
| 2,854,978 A | 10/1958 | Millman et al. | ............. | 128/285 |
| 2,876,496 A | 3/1959 | Murphy, Jr. | ............. | 18/56 |
| 3,032,036 A | 5/1962 | Rader et al. | ............. | 128/263 |
| 3,055,369 A | 9/1962 | Graham, Jr. | ............. | 128/285 |
| 3,068,867 A | 12/1962 | Bletzinger et al. | ............. | 128/285 |
| 3,102,540 A | 9/1963 | Bentov | ............. | 128/232 |
| D197,751 S * | 3/1964 | Rigney et al. | ............. | D24/114 |
| 3,139,886 A | 7/1964 | Tallman et al. | ............. | 128/263 |
| 3,320,956 A | 5/1967 | Steiger | ............. | 128/263 |
| 3,340,874 A | 9/1967 | Burgeni | ............. | 128/285 |
| 3,433,225 A | 3/1969 | Voss et al. | ............. | 128/263 |
| 3,628,533 A | 12/1971 | Loyer | ............. | 128/263 |
| 3,807,399 A | 4/1974 | Morman et al. | ............. | 128/263 |
| 3,918,452 A | 11/1975 | Cornfeld | ............. | 128/270 |
| 3,929,960 A | 12/1975 | Findlay et al. | ............. | 264/292 |
| 4,048,998 A | 9/1977 | Nigro | ............. | 128/263 |
| 4,148,317 A | 4/1979 | Loyer | ............. | 128/263 |
| 4,177,237 A | 12/1979 | Ueno et al. | ............. | 264/296 |
| 4,198,978 A | 4/1980 | Nigro | ............. | 128/285 |
| 4,273,125 A | 6/1981 | Sakurai | ............. | 128/263 |
| 4,286,595 A | 9/1981 | Ring | ............. | 128/263 |
| 4,318,405 A | 3/1982 | Sneider | ............. | 128/263 |
| 4,354,495 A | 10/1982 | Bodicky | ............. | 128/348 |
| 4,398,532 A | 8/1983 | Sweeney, III | ............. | 128/127 |
| 4,447,199 A | 5/1984 | Reed et al. | ............. | 425/182 |
| 4,447,222 A | 5/1984 | Sartinoranont | ............. | 604/15 |

(Continued)

FOREIGN PATENT DOCUMENTS

EP  0355396  7/1989

(Continued)

*Primary Examiner*—Tatyana Zalukaeva
*Assistant Examiner*—Ginger T. Chapman
(74) *Attorney, Agent, or Firm*—Ohlandt, Greeley, Ruggiero & Perle, L.L.P.

(57) ABSTRACT

A plunger having a first end, a second end, and a main body is provided. The first end of the plunger is about 10% to about 15% larger than the main body and the second end is more than about 50% larger than the main body.

3 Claims, 3 Drawing Sheets

U.S. PATENT DOCUMENTS

| | | | | |
|---|---|---|---|---|
| 4,475,911 | A | 10/1984 | Gellert | 604/367 |
| 4,496,341 | A | 1/1985 | Brucks | 604/14 |
| 4,536,178 | A | 8/1985 | Lichstein et al. | 604/15 |
| 4,547,416 | A | 10/1985 | Reed et al. | 428/36 |
| 4,551,292 | A | 11/1985 | Fletcher et al. | 264/139 |
| 4,592,740 | A | 6/1986 | Mahruki | 604/15 |
| 4,699,610 | A | 10/1987 | Hanano et al. | 604/16 |
| 4,726,805 | A | 2/1988 | Sanders, III | 604/15 |
| 4,735,538 | A | 4/1988 | Reed et al. | 413/5 |
| 4,806,182 | A | 2/1989 | Rydell et al. | 156/211 |
| 4,846,802 | A | 7/1989 | Sanders, III | 604/15 |
| 4,895,559 | A | 1/1990 | Shippert | 604/15 |
| 4,921,474 | A | 5/1990 | Suzuki et al. | 604/16 |
| 4,960,417 | A | 10/1990 | Tarr, Jr. et al. | 604/15 |
| 5,078,702 | A | 1/1992 | Pomeranz | 604/280 |
| 5,135,475 | A | 8/1992 | Nakanishi et al. | 604/14 |
| 5,153,971 | A | 10/1992 | Van Iten | 28/118 |
| 5,158,535 | A | 10/1992 | Paul et al. | 604/15 |
| 5,215,694 | A | 6/1993 | Bartimes et al. | 264/68 |
| 5,267,953 | A | 12/1993 | Paul et al. | 604/15 |
| 5,389,068 | A | 2/1995 | Keck | 604/15 |
| 5,395,308 | A | 3/1995 | Fox et al. | 604/15 |
| 5,397,312 | A | 3/1995 | Rademaker et al. | 604/218 |
| 5,437,628 | A | 8/1995 | Fox et al. | 604/14 |
| 5,447,499 | A | 9/1995 | Allaire et al. | 602/42 |
| 5,531,674 | A | 7/1996 | Frayman | 604/11 |
| 5,533,966 | A | 7/1996 | Schoelling | 604/18 |
| 5,533,990 | A | 7/1996 | Yeo | 604/363 |
| 5,547,701 | A | 8/1996 | Nielsen et al. | 427/2.3 |
| 5,571,181 | A | 11/1996 | Li | 623/11 |
| 5,571,540 | A | 11/1996 | Weyenberg et al. | 425/343 |
| 5,614,230 | A | 3/1997 | Weyenberg et al. | 425/393 |
| 5,659,934 | A | 8/1997 | Jessup et al. | 28/120 |
| 5,662,601 | A | 9/1997 | Snead | 604/15 |
| 5,683,358 | A | 11/1997 | Nielsen et al. | 604/11 |
| 5,716,572 | A | 2/1998 | Lesiczka et al. | 264/161 |
| 5,738,646 | A | 4/1998 | Fox et al. | 604/15 |
| 5,746,710 | A | 5/1998 | Nielsen et al. | 609/14 |
| 5,782,793 | A | 7/1998 | Nielsen et al. | 604/14 |
| 5,792,096 | A | 8/1998 | Rentmeester et al. | 604/14 |
| 5,795,320 | A | 8/1998 | Nielsen et al. | 604/12 |
| 5,817,047 | A | 10/1998 | Osborn, III et al. | 604/14 |
| 5,827,467 | A | 10/1998 | Ruppert et al. | 264/322 |
| 5,873,971 | A | 2/1999 | Balzar | 156/217 |
| 5,958,321 | A | 9/1999 | Schoelling et al. | 264/318 |
| D415,565 | S | 10/1999 | Hayes et al. | D24/141 |
| 5,984,888 | A | 11/1999 | Nielsen et al. | 604/12 |
| 6,019,744 | A | 2/2000 | Altdorf et al. | 604/16 |
| 6,036,666 | A | 3/2000 | Peiler et al. | 604/11 |
| 6,068,899 | A | 5/2000 | Osborn, III et al. | 428/35.2 |
| 6,126,886 | A | 10/2000 | Beck et al. | 264/521 |
| D436,661 | S | 1/2001 | Berry | D24/141 |
| 6,168,576 | B1 | 1/2001 | Reynolds | 604/15 |
| 6,190,348 | B1 | 2/2001 | Tiemann et al. | 604/15 |
| 6,217,542 | B1 | 4/2001 | Stevens et al. | 604/17 |
| 6,296,633 | B1 | 10/2001 | Helgerson | 606/1 |
| 6,355,011 | B1 | 3/2002 | Suga | 604/15 |
| 6,364,852 | B1 | 4/2002 | Lee | 604/15 |
| 6,364,854 | B1 | 4/2002 | Ferrer et al. | 604/60 |
| 6,432,075 | B1 | 8/2002 | Wada et al. | 604/15 |
| 6,432,076 | B1 | 8/2002 | Wada et al. | 604/15 |
| 6,450,986 | B1 | 9/2002 | Binner et al. | 604/15 |
| 6,478,764 | B1 | 11/2002 | Suga | 604/15 |
| 6,508,780 | B1 * | 1/2003 | Edgett et al. | 604/15 |
| 2003/0040695 | A1 | 2/2003 | Zhao et al. | 604/15 |
| 2003/0045829 | A1 | 3/2003 | Gehling et al. | 604/11 |
| 2004/0054317 | A1 * | 3/2004 | Lemay et al. | 604/15 |

FOREIGN PATENT DOCUMENTS

| | | |
|---|---|---|
| EP | 1040808 | 3/2000 |
| EP | 1101472 | 5/2001 |
| EP | 1101473 | 5/2001 |
| FR | 2639833 | 6/2000 |
| JP | 584263 | 4/1993 |
| JP | 2000279445 | 10/2000 |
| JP | 2000279446 | 10/2000 |
| JP | 2001473 | 1/2001 |
| JP | 2001145657 | 5/2001 |
| JP | 2001145658 | 5/2001 |
| WO | WO 89/04159 | 5/1989 |
| WO | WO 96/20684 | 7/1996 |

* cited by examiner

TAMPON APPLICATOR ASSEMBLY HAVING AN IMPROVED PLUNGER AND METHODS OF MAKING

BACKGROUND OF THE INVENTION

1. Field of the Invention

The present invention is related to a tampon applicator assembly. More particularly, the present invention is related to a tampon applicator assembly having an improved plunger that increases the ease of use and user comfort. Further, the present invention is related to methods of making such an improved plunger.

2. Description of Related Art

A tampon applicator assembly is used to inject an absorbent or hygienic material, known as a tampon pledget, into a vaginal cavity. Commercial tampon applicator assemblies typically have a barrel and a plunger used to expel a pledget housed in the barrel.

The use of such tampon assemblies requires a user to grip the barrel, guide it easily into the vaginal cavity, and apply a pressure to the plunger to expel the pledget from the barrel. A portion or all of the assembly is out of a direct line of sight of the user during this process. Accordingly, assemblies that are difficult to grip and control can hinder proper and comfortable delivery of the pledget.

Another problem associated with a difficult to grip and control assembly is that the user often applies excessive gripping force on the barrel and/or on the plunger to compensate for the lack of gripability. This excessive force may result in discomfort to the user during delivery of the pledget.

Many factors combine to increase the comfort of the user during the use of a tampon applicator assembly. For example, the user's comfort can be affected by with one or more ease factors. These ease factors can in the ease with which: the assembly is inserted into the vagina, the pledget is expelled from the assembly, and the spent assembly is removed from the vagina. Thus, there is a need to provide improved plungers for a tampon applicator assembly, which increases the user's comfort by addressing one or more of the aforementioned ease factors.

BRIEF SUMMARY OF THE INVENTION

It is an object of the present invention to provide an improved tampon applicator plunger, which is easy to grip and control during expulsion of the pledget.

It is another object to provide a plunger for a tampon applicator assembly, where the plunger has tapered ends to facilitate expulsion of the pledget.

It is a further object to provide a method of making an improved plunger for a tampon applicator assembly.

These and other objects of the present invention are provided by a tampon applicator assembly having a plunger with a first end, a second end, and a main body. The first end is about 10% to about 15% larger than the main body and the second end is more than about 50% larger than the main body.

The present invention also provides a method of forming a plunger for a tampon applicator assembly. The method includes forming a segment of extruded tubing having a first end, a main body, and a second end; flaring the first end of the segment; and flaring the second end of the segment.

A method of forming a plunger for a tampon applicator assembly is also provided by cutting an extruded tube into a plurality of segments; inserting one segment of the plurality of segments into a barrel of the tampon applicator assembly so that a main body of the segment is slidably received in the barrel; and deforming simultaneously a first end of the segment and a second end of the segment.

The above-described and other features and advantages of the present invention will be appreciated and understood by those skilled in the art from the following detailed description, drawings, and appended claims

DETAILED DESCRIPTION OF THE INVENTION

Figure 1:
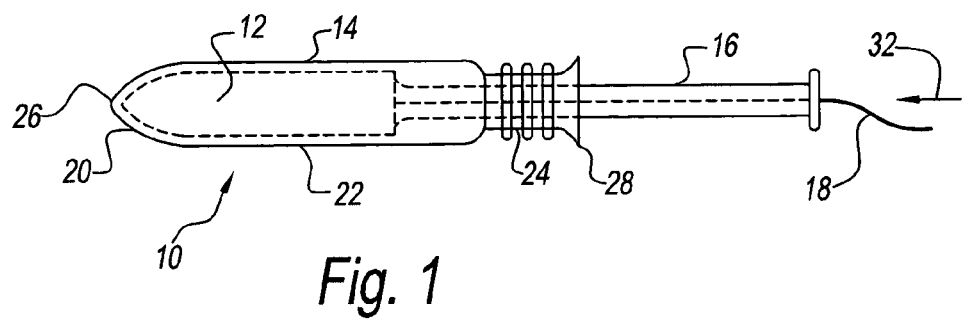
FIG. 1 is a side view of an exemplary embodiment of a tampon applicator assembly according to the present invention.
Figure 2:
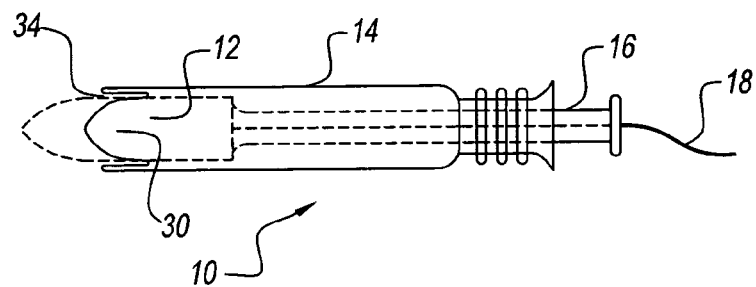
FIG. 2 is a side view of the assembly of FIG. 1 during expulsion of the pledget.

Referring now to the figures and more particularly to FIGS. 1 and 2, an exemplary embodiment of a tampon applicator assembly generally represented by reference numeral 10 is illustrated. Assembly 10 is easier to insert, use, and remove than prior assemblies.

Assembly 10 has a pledget 12, a barrel 14, and a plunger 16. Pledget 12 is disposed in barrel 14. Pledget 12 has a withdrawal cord 18 connected thereto, which extends through barrel 14 and plunger 16, and out of assembly 10.

Barrel 14 is sub-divided into three sections, namely an insertion tip 20, a main section 22, and a finger grip 24. Insertion tip 20 defines a insertion end 26 of barrel 14, while finger grip 24 terminates at a gripping end 28 of the barrel.

Plunger 16 can expel pledget 12 from barrel 14. For example, insertion end 26 can have a number or plurality of petals 30 disposed about the end. Petals 30 open (FIG. 2) upon application of a predetermined expulsion force by pledget 12. Plunger 16 is slidably disposed in barrel 14 at gripping end 28. Pledget 12 is expelled through insertion end 26 through the movement of plunger 16 in the direction of arrow 32. As plunger 16 is moved in the direction of arrow 32, the plunger urges pledget 12 into petals 30 until the petals open and can continue until the pledget is expelled from barrel 14 through insertion end 26.

Petals 30 are defined in insertion tip 20 by a number or plurality of slits 34. It should be recognized that insertion tip 20 of barrel 14 is illustrated by way of example only as having four petals 30. Of course, insertion tip 20 having more or less than four petals 30 is contemplated by the present invention. For example, insertion tip 20 can have about 2 to about 6 petals, preferably about 3 to about 5 petals, more preferably about 4 petals.

When in a closed position (FIG. 1), petals 30 collectively provide insertion tip 20 with a shape that facilitates insertion. It has also been determined that providing assembly 10 with finger grip 24 can enhance the actual and perceived level of comfort associated with inserting barrel 14 of assembly 10, expelling pledget 12 from the barrel, and removing the barrel.

Figure 3:
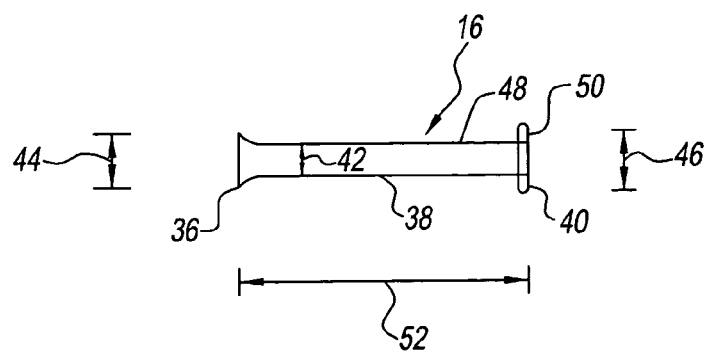
FIG. 3 is a side view of the plunger of FIGS. 1 and 2.
Figure 4:
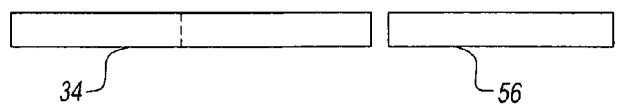
FIGS. 4 through 7 illustrate an exemplary embodiment of a method of forming the plunger of FIG. 3.
Figure 5:
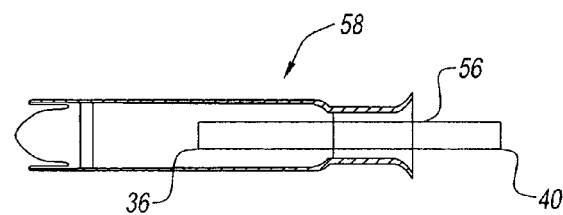

Plunger 16 is described with reference to FIG. 3. Plunger 16 has a first end 36, a main body 38, and a second end 40.

In use, a user applies a force on second end 40 to move plunger 16 in barrel 14 as described above so that first end 36 acts on pledget 12.

First end 36 facilitates distribution of force from plunger 16 to pledget 12. Additionally, first end 36 prevents plunger 16 from separating from barrel 16 through gripping end 28. Accordingly, first end 36 is flared or trumpeted to an outer dimension 44, which is larger than an outer dimension 42 of main body 38 and larger than the smallest inner dimension of finger grip 24. Preferably, outer dimension 44 is about 10% to about 25% larger than outer dimension 42, more preferably about 15% larger than outer dimension 42.

Preferably, assembly 10 has a circular cross section in which dimensions 42, 44 are diameters. Of course, it is contemplated by the present invention for assembly 10 to can have any cross sectional shape, such as circular and non-circular including oval and polygonal shapes. Furthermore, it is contemplated that the cross sectional shape can vary along the length of barrel 14 and/or plunger 16. For example, plunger 16 can have a circular first end 36, a polygonal main body 38, and an ovoid second end 40.

Second end 40 has an outer dimension 46, which is sized to receive the finger of a user. Accordingly, outer dimension 46 is preferably larger than outer dimension 42 of main body 38. This larger outer dimension 46 provides the user with a broader area on which to push plunger 16, giving the user more control and comfort upon insertion.

Outer dimension 46 can be at least about 22% larger than outer dimension 42 of main body 36, preferably outer dimension 46 is more than about 50% larger than outer dimension 42, more preferably about 85% larger. For example, outer dimension 42 of main body 36 can be about 0.175 inches. In this example, outer dimension 46 of second end 40 can be at least about 0.22 inches, preferably about 0.26 inches, more preferably about 0.325 inches.

Table 1 below illustrates various dimensions of prior art plungers.

TABLE 1

| Brand | Plunger main body outer dimension (inches) | Plunger second end outer dimension (inches) | % Larger |
|---|---|---|---|
| Competitor Regular/Super/Super Plus | 0.271 | 0.303 | 11.8% |
| Kotex Regular | 0.539 | 0.651 | 20.8% |
| Kotex Super/Super Plus | 0.635 | 0.755 | 18.9% |
| Rely Regular | 0.564 | 0.675 | 19.7% |
| Unicharm | 0.163 | 0.301 | 48.7% |

As Table 1 illustrates, outer dimension 46 is larger than outer dimension 42 by a significantly greater amount than previously available.

The increase from outer dimension 42 to outer dimension 46 can be a gradual increase, such as a trumpeting or flaring of plunger 16. Alternately, the increase from outer dimension 42 to outer dimension 46 can be an abrupt ledge at second end 40 of plunger 16. In addition, second end 40 of plunger 16 can be rolled or can be squared off.

Preferably, second end 40 has both a flare 48 and a roll 50 formed therein. Second end 40 having both flare 48 and roll 50 has increased strength as compared to a simple flared end, and offers increased gripping area as compared to a simple rolled end.

Plunger 16 can have an overall length 52 of about 1 inch to 4 inches, preferably overall length 50 is about 2.25 inches to about 3 inches. Main body 38 can have a cross-sectional shape and outer dimension 42, which is received in barrel 14 at gripping end 28. In addition, it is preferred that outer dimension 42 of main body 38 be constant along the length of the main body to facilitate the transmission force from second end 40 to first end 36. Preferably, plunger 16 has a uniform cross-sectional shape and a uniform outer dimension 42 along least two-thirds of length 50.

Referring now to FIGS. 4 through 7, an exemplary embodiment of a method of forming plunger 16 according to the present invention is illustrated. Plunger 16 is initially formed as a long length of extruded tube 54. By way of example, plunger 16 can be extruded from high-density polyethylene (HDPE). Subsequently, extruded tube 54 is cut to size to form a number or plurality of extruded segments 56.

Figure 6:
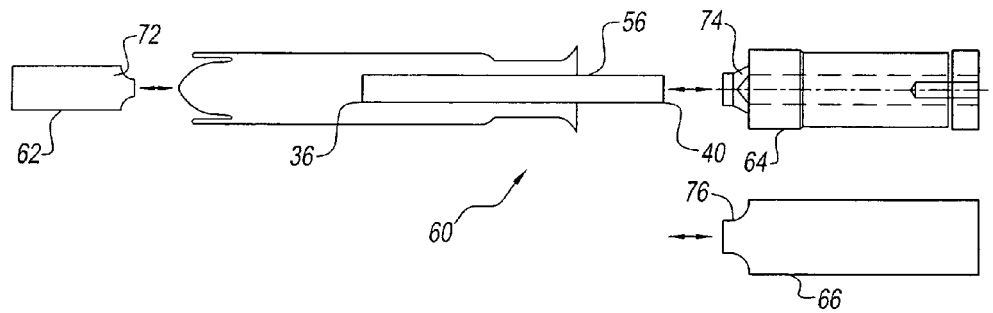
Figure 7:
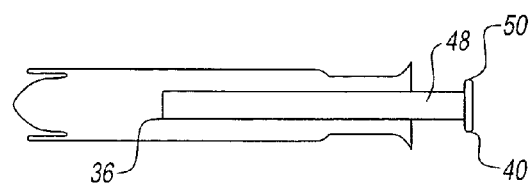

Segment 56 is disposed in barrel 14 to form a subassembly 58. Segment 56 can be inserted into barrel 14 through either insertion end 26 or gripping end 28 of the barrel. Subassembly 58 is exposed to a post extrusion operation 60 as illustrated in FIG. 6 to form plunger 16 from segment 56.

Operation 60 uses a first mandrel 62, a second mandrel 64, and a third mandrel 66 to form plunger 16. First mandrel 62 has a forming end 72 dimensioned to form the flare on first end 36 of plunger 16. Second mandrel 64 has a forming end 74 dimensioned to form flare 48 and roll 50 in second end 40 of plunger 16.

During post extrusion operation 60, first and second mandrels 62, 64 are heated to about 210 degrees Fahrenheit (F) to about 230 degrees F., more preferably about 220 degrees F. First and second mandrels 62, 64 are then brought into contact with plunger 16 for about 1 second to about 3 seconds, more preferably about 2 seconds. Since first and second mandrels 62, 64 are heated to a temperature close to the melting temperature of plunger 16, the mandrels cause the plunger to soften and to conform to the shape of the mandrels, respectively. Therefore, first mandrel 62 flares first end 36, while second mandrel 64 forms flare 48 and roll 50 in second end 40.

It has been found that a third mandrel 66 can he used to cool and set the material of second end 40 while holding second end 40 at the desired larger outer dimension 46 of flare 48. Third mandrel 66 has a forming end 76 that is preferably identical to forming end 74, and which is maintained at about 65 degrees F. to about 75 degrees F., more preferably about 70 degrees F.

It should be recognized that the aforementioned times and temperatures are representative of plunger 16 made from high-density polyethylene (HDPE). Of course, larger and/or smaller times and/or temperatures are contemplated by the present invention.

Third mandrel 66 is inserted into second end 40 after second mandrel 64 has been removed from the second end. Third mandrel 66 is contacted with second end 40 of plunger for about 1 second to about 3 seconds, more preferably about 2 seconds. Third mandrel 66 maintains flare 48 and roll 50 in the desired shape while the reduced temperature of the third mandrel sets the material of second end 40 in the desired shape.

The dwell time of post extrusion operation 60 to remove second mandrel 64 and contact third mandrel 66 is preferably about 0.5 seconds to about 1.5 seconds, more preferably about 1 second. Thus, operation 60 preferably has an overall cycle time of about 2.5 seconds to about 7.5 seconds, more preferably about 5 seconds.

In a less preferred embodiment, second mandrel 64 can be a heatable/coolable mandrel and, thus, can take the place of third mandrel 66. Here, second mandrel 64 remains in contact with second end 40 while it is cooled to the desired temperature. Next, second mandrel 64 is contacted with second end 40 of plunger for about 1 second to about 3 seconds, more preferably about 2 seconds. In this embodiment, second mandrel 64 maintains flare 48 and roll 50 in the desired shape while the reduced temperature sets the material of second end 40 in the desired shape.

It has been determined that operation 60 advantageously forms plunger 16 having the desired flare 48 and roll 50 without the cost and time associated with the complex molding operations as would otherwise be necessary. In addition, operation 60 can be used to retrofit current manufacturing processes to simply and easily provide plunger with a roll and a flare on second end 40.

Figure 8:
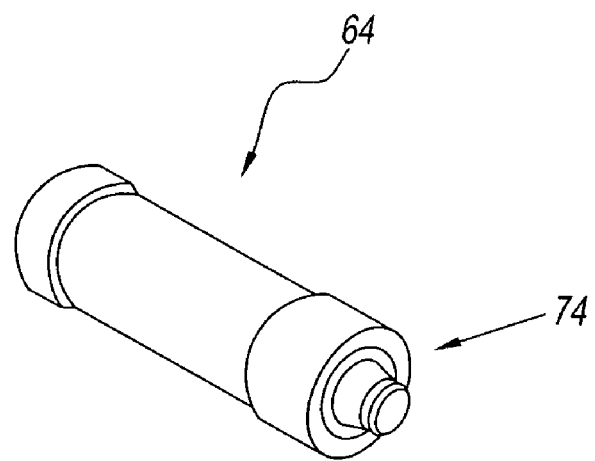
FIGS. 8 and 9 illustrate an exemplary embodiment of the second mandrel of FIG. 6.
Figure 9:
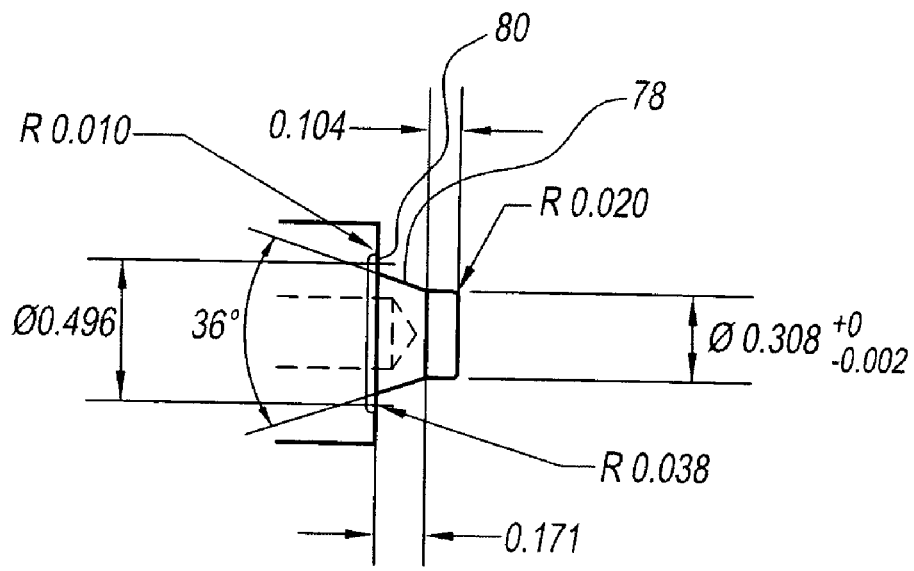

An exemplary embodiment of second mandrel 64 of the present invention is illustrated in FIGS. 8 and 9. Forming end 74 of second mandrel 64 has a flaring portion 78 and a rolling portion 80. Flaring portion 78 is dimensioned to provide second end 40 with flare 48 having outer dimension 46. Rolling portion 80 is dimensioned to roll second end 40 and, thus, is dimensioned to form roll 50. Again, third mandrel 66 can have an identical forming end 76 as forming end 74 described above.

By way of example, plunger 16 is described as being formed of high-density polyethylene (HDPE). Of course, it is contemplated by the present invention for plunger 16 to be formed of any plastic material, paper material, or any combinations thereof.

Assembly 10 provides a combination of features, which achieve consumer benefits unavailable in prior assemblies. For example, the combination of the petal ratio, the length-to-width ratio of petals 30, and the outer dimensions of first and second ends 36, 40 of plunger 16, all combine to increase the ease and comfort of expelling pledget 12 from barrel 14.

It should also be noted that the terms "first", "second", "third", "upper", "lower" and the like may be used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the invention. In addition, many modifications may be made to adapt a particular situation or material to the teachings of the disclosure without departing from the scope thereof. Therefore, it is intended that the present invention not be limited to the particular embodiment(s) disclosed as the best mode contemplated for carrying out this invention, but that the present invention will include all embodiments falling within the scope of the appended claims.

What is claimed is:

1. A tampon applicator assembly comprising:
   a barrel having a main section disposed between an insertion tip and a finger grip;
   a plunger having a first end, a main body, and a second end, said plunger being slideably received in said barrel; and
   a pledget disposed in said barrel between said insertion tip and said first end of said plunger so that a force applied on said second end of said plunger expels said pledget from said barrel at said insertion end,
   wherein said first end of said plunger has a first outer dimension, said second end has a second outer dimension, and wherein said main body has a third outer dimension, said first outer dimension is about 10% to about 15% larger than said third outer dimension and said second outer dimension is more than about 85% larger than said third outer dimension.

2. The assembly as in claim 1, wherein said first outer dimension is about 15% larger than said third outer dimension.

3. The assembly as in claim 1, wherein said main section of said barrel has a maximum outer dimension located closer to said finger grip than to said insertion tip.

* * * * *